(12) United States Patent
Grahek et al.

(10) Patent No.: US 7,141,602 B2
(45) Date of Patent: Nov. 28, 2006

(54) PROCESS FOR OBTAINING HMG-COA REDUCTASE INHIBITORS OF HIGH PURITY

(75) Inventors: Rok Grahek, Kranj (SI); Dusan Milivojevic, Ljubljana (SI); Andrej Bastarda, Vrhnika (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 87 days.

(21) Appl. No.: 10/698,009

(22) Filed: Oct. 30, 2003

(65) Prior Publication Data

US 2004/0138294 A1 Jul. 15, 2004

Related U.S. Application Data

(63) Continuation-in-part of application No. 09/720,952, filed as application No. PCT/IB99/01553 on Sep. 17, 1999, now Pat. No. 6,695,969.

(30) Foreign Application Priority Data

Sep. 18, 1998 (SI) .................................... 9800241

(51) Int. Cl.
*A61K 31/351* (2006.01)
*C07D 309/30* (2006.01)

(52) U.S. Cl. ...................... 514/460; 549/263; 549/273; 549/292; 514/451

(58) Field of Classification Search ................ 549/263, 549/292; 514/449, 460; 210/656
See application file for complete search history.

(56) References Cited

U.S. PATENT DOCUMENTS

| | | | | |
|---|---|---|---|---|
| 4,231,938 A | | 11/1980 | Monaghan | 260/343.5 |
| 5,043,423 A | | 8/1991 | Viscomi et al. | 530/344 |
| 5,202,029 A | | 4/1993 | Haytko et al. | 210/656 |
| 5,420,024 A | | 5/1995 | Carta et al. | 435/125 |
| 5,427,686 A | | 6/1995 | Asher | 210/635 |
| 5,622,985 A | * | 4/1997 | Olukotun et al. | 514/423 |
| 5,798,375 A | * | 8/1998 | Tsujita et al. | 514/369 |
| 6,159,997 A | * | 12/2000 | Tsujita et al. | 514/369 |
| 6,218,403 B1 | * | 4/2001 | Daste et al. | 514/301 |
| 6,268,186 B1 | | 7/2001 | Sibeijn et al. | 435/125 |
| 6,689,590 B1 | | 2/2004 | Keri et al. | 435/135 |
| 6,695,969 B1 | * | 2/2004 | Grahek et al. | 210/656 |
| 6,936,731 B1 | | 8/2005 | Keri et al. | 560/256 |

FOREIGN PATENT DOCUMENTS

| | | |
|---|---|---|
| EP | 0 416 416 A1 | 3/1991 |
| WO | WO 92/16276 | 10/1992 |

OTHER PUBLICATIONS

Horváth, Displacement Chromatography: Yesterday, Today and Tomorrow, Journal of Chromatography Library, vol. 32, pp. 179-203. 1985.
Brian Bidlingmeyer, Preparative Liquid Chromatography, Journal of Chromatography Library, vol. 38, pp. 12-13, 1987.
Cramer at al., Tandem use of Carboxypeptidase Y. Reactor and Displacement Chromatography for Peptide Synthesis, Journal of Chromatography, vol. 394, pp. 305-314 (1987).
Subramanian et al., Displacement Chromatography of Biomolecules, Journal of Chromatography, vol. 439, pp. 341-351 (1988).
Gu et al., Displacement Effect in Multicomponent Chromatography, AIChE Journal, vol. 36, pp. 1156-1162 (1990).
Felinger et al., Optimization of the experimental conditions and the column design partners in displacement chromatography, Journal of Chromatography vol. 609, pp. 35-47, (1992).
Frenz, Frontiers of Biopolymer Purification: Displacement Chromatography, LC-GC International, vol. 5, pp. 18-21, (1992).
Guiochon et al., Fundamentals of Preparative and Nonlinear Chromatography, pp. 301-303, Academic Press, © 1994.
Grahek et al., Chromatographic Purification of SINEGMG-CoA Reductase Inhibitors, Lek dd. Research and Development.
PCT/IB 99/01553 International Search Report.
Arai, et al., *Pravastatin Sodium(CS-514), A Novel Cholesterol Lowering Agent Which Inhibits HMG-CoA Reductase*, Annu. Rep. Sankyo Res. Lab., 40; 1-38, 1988.

* cited by examiner

*Primary Examiner*—Golam M. M. Shameem
(74) *Attorney, Agent, or Firm*—Bromberg & Sunstein LLP

(57) ABSTRACT

Lovastatin, pravastatin, simvastatin, mevastatin, atorvastatin, and derivatives and analogs thereof are known as HMG-CoA reductase inhibitors and are used as antihypercholesterolemic agents. The majority of them are produced by fermentation using microorganisms of different species identified as species belonging to *Aspergillus, Monascus, Nocardia, Amycolatopsis, Mucor* or *Penicillium* genus, *Streptomyces, Actinomadura, Micromonospora*, some are obtained by treating the fermentation products using the method of chemical synthesis or they are the products of total chemical synthesis. The purity of the active ingredient is an important factor for manufacturing the safe and effective pharmaceutical, especially if the pharmaceutical product must be taken on a longer term basis in the treatment or prevention of high plasma cholesterol. The accumulation of the impurities from the pharmaceuticals of lower purity may cause many side effects during the medical treatment. The present invention relates to a new industrial process for the isolation of HMG-CoA reductase inhibitors using so-called displacement chromatography. Use of the invention enables one to obtain HMG-CoA reductase inhibitors of high purity, with high yields, lower production costs and suitable ecological balance.

5 Claims, No Drawings

PROCESS FOR OBTAINING HMG-CoA REDUCTASE INHIBITORS OF HIGH PURITY

CROSS REFERENCE TO RELATED APPLICATIONS

This application is a continuation-in-part application from U.S. patent application Ser. No. 09/720,952, filed Jan. 3, 2001, now U.S. Pat. No. 6,695,969 based on PCT application no. PCT/IB99/01553, which has an international filing date of Sep. 17, 1999, both of which are hereby incorporated by reference herein.

TECHNICAL FIELD AND BACKGROUND ART

The present invention involves a process for the purification of HMG-CoA reductase inhibitors and relates to purified HMG-CoA reductase inhibitors.

Lovastatin, pravastatin, simvastatin, mevastatin, atorvastatin and derivatives and analogs thereof are known as HMG-CoA reductase inhibitors and are used as antihypercholesterolemic agents. The majority. of them are produced by fermentation using microorganisms of different species identified as species belonging to *Aspergillus, Monascus, Nocardia, Amycolatopsis, Mucor* or *Penicillium* genus, *Streptomyces, Actinomadura, Micromonospora*, some are obtained by treating the fermentation products using the method of chemical synthesis or they are the products of total chemical synthesis.

The purity of the active ingredient is an important factor for manufacturing the safe and effective pharmaceutical, especially if the pharmaceutical product must be taken on a longer term basis in the treatment or prevention of high plasma cholesterol. The accumulation of the impurities from the pharmaceuticals of lower purity may cause many side effects during the medical treatment.

The present invention relates to a new industrial process for the isolation of HMG-CoA reductase inhibitors using so-called displacement chromatography. Use of the invention enables to obtain HMG-CoA reductase inhibitors of high purity, with high yields, lower production costs and suitable ecological balance.

BACKGROUND OF THE INVENTION

The processes for the isolation and purification of antihypercholesterolemic agents disclosed in the earlier patent documents include a variety of combinations of extraction, chromatography, lactonization and crystallization methods.

The purity of the final product obtained by these procedures complies with the USP standards but the yields of the desired product are relatively low. In addition, they require both large amounts of organic solvents and the large equipment suited for these quantities. The isolation process disclosed in WO 92/16276 provides the solution for obtaining HMG-CoA reductase inhibitors of purity greater than 99.5% with the use of industrial HPLC (high performance liquid chromatography) equipment.

According to WO 92/16276 the crude HMG-CoA reductase inhibitor, with a purity of $\geq 85\%$, is dissolved in an organic solvent or in a solution of organic solvent and water. The mixture is then buffered to a pH between 2 and 9 and placed on the HPLC column. After the HMG-CoA reductase inhibitor peak of interest is collected, a portion of solvent is removed and the water is added or alternatively two-thirds of the solvent mixture is removed and the HMG-CoA reductase inhibitor is crystallized. At the end, the purity of the product obtained by this process is at least 99.5% with the yield of around 90%.

The method disclosed in WO 92/16276 enables obtaining of HMG-CoA reductase inhibitors of high purity, with relatively high yields, the disadvantage of the method over the conventional chromatography columns are relatively small quantities of the substance loaded per HPLC column. Small samples to be fed into the column are also related with increased number of repetitions of the isolation operations in order to obtain sufficient quantities of the desired substance, and consequently large amount of the solvents used resulting in higher production costs.

Displacement chromatography method is the basis of the present invention. Displacement chromatography is based on competition of the components of the sample fed into the column for active sites on the stationary phase. Individual components of the sample displace one another like a train, the displacer, having the very high affinity for the stationary phase and travelling behind the fed sample along the column, drives the separation of the sample components into one-compartment zones which move at the same velocity as the displacer. Concentrating of individual components is carried out simultaneously with the purification.

The principle of displacement chromatography method is relatively old as it has been known since 1943 but it was introduced into practice as late as 1981 because of the lack of efficient columns (Cs. Horvath et al., J. Chromatogr., 215 (1981) 295; J. Chromatogr., 330 (1985) 1; J. Chromatogr., 440 (1988) 157). These papers, introduced herein by way of reference, describe the analytic and preparative separation and purification of biologically active peptides and polymyxin antibiotics (polypeptides) using reversed-phase high performance liquid chromatography columns in the displacement mode. For polymyxins octadecyl silica gel columns 250×4.6 mm, particle size 5 µm, 10% acetonitrile in water as the mobile phase and different tetraalkylammonium halogenides as the displacer were used.

In recent investigations in the field of displacement chromatography (S. M. Cramer et al., Enzyme Microb. Technol., 11 (1989) 74; Prep. Chromatogr., 1 (1988) 29; J. Chromatogr., 394 (1987) 305; J. Chromatogr., 439 (1988); J. Chromatogr., 454 (1988) 1 (theoretic optimisation)); A. Felinger et al., J. Chromatogr., 609 (1992) 35 (theoretic optimisation), all papers being introduced herein by way of reference) similar columns were used; the mobile phase was methanol in the phosphate buffer, the displacer was 2-(2-t-butoxyethoxy)ethanol (BEE) in acetonitrile and sodium acetate. Different peptides, proteins and cephalosporin C antibiotic were used as the samples.

U.S. Pat. No. 5,043,432 and EP 416.416 respectively, describe the method for purifying certain low molecular (below 1000 daltons) peptides (in particular, tuftsin and synthetic derivatives thereof) with displacement ion-exchange chromatography where the stationary phase used is cationic-exchange resin, the transporter solvent is water or dilute solutions of a variety of strong acids, and the displacer used is triethylenetetraammonuim salt in different concentrations.

In U.S. patent application Ser. No. 08/875,422, yet unpublished, the use of displacement chromatography for the isolation and purification of vancomycin is described.

WO 02/32848 (equivalent EP 1327626) describes a process for the isolation or purification of pravastatin or a pharmacologically acceptable salt thereof by carrying out a step of extracting pravastatin and analogues thereof using an organic solvent having formula $CH_3CO_2R$ (wherein R represents an alkyl group having three or more carbons) and/or by decomposing the impurities by use of an inorganic acid and/or by use of an inorganic base.

Disclosed is also a composition comprising pravastatin sodium which is industrially produced, wherein a compound having formula (I), which is namely epipravastatin sodium, is contained in an amount of 0.1% or less by weight of pravastatin sodium.

WO 02/30415 describes pravastatin sodium substantially free of pravastatin lactone and epiprava, the C-6 epimer of pravastatin. Described are also pravastatin sodium containing less than 0.5% of pravastatin lactone and/or less than 0.2% of epiprava and pravastatin sodium containing less than 0.2% of pravastatin lactone and/or less than 0.1% of epiprava. It also discloses a process for the preparation of such a pravastatin sodium that involves extraction of pravastatin from an aqueous fermentation broth into an organic solvent, back-extraction of pravastatin into a basic aqueous solution and a re-extraction into an organic solvent, resulting in an organic solution that is enriched in pravastatin relative to the initial concentration of pravastatin in the fermentation broth. Pravastatin is then obtained from the enriched solution by precipitation as its ammonium salt, followed by purification by recrystallization of the ammonium salt and transposition of this salt into pravastatin sodium salt, which is isolated in a highly pure state from solution by recrystallization, lyophilization or other means.

A similar process is described in U.S. Pat. No. 6,444,452. The disclosed process of isolating and/or purifying a statin compound from an aqueous fermentation broth on an industrial preparative scale applies no chromatographic separation. Among the statins described are pravastatin, compactin and lovastatin. The disclosed process involves extraction of pravastatin from an aqueous fermentation broth into an organic solvent, back-extraction of pravastatin into a basic aqueous solution and, optionally, a re-extraction into an organic solvent or concentration of the aqueous solution, resulting in either an aqueous or organic solution that is enriched in pravastatin relative to the initial concentration of pravastatin in the fermentation broth. The pravastatin obtained from the enriched solution by precipitation of its metal or ammonium salt is then purified by recrystallization and the recrystallized salt is then trans-salified to form pravastatin sodium salt. The sodium salt of pravastatin is then isolated from the solution by recrystallization, lyophilization or other means.

Disclosed is also pravastatin in a highly pure form with a purity of about 99.3% to 99.8% and with a yield in the range from 34% to 72%.

U.S. Pat. No. 6,387,258 discloses a process for obtaining highly purified crystals of statin compounds from a fermentation broth, which is useful for purifying compactin, pravastatin and lovastatin. The process disclosed involves the steps of: (i) pretreating the fermentation broth under alkaline conditions to remove non-polar impurities; (ii) extracting the statin under acidic conditions as a hydroxy acid or a lactone from the fermentation broth into a hydrophobic organic extraction solvent; (iii) separating the hydrophobic organic extraction solvent from the fermentation broth; (iv) concentrating the hydrophobic organic extraction solvent containing the extracted statin compound while forming the lactone; and (v) purifying the extracted statin compound by crystallization. Disclosed are compactin with a purity of 98.7% w/w, 99.0% w/w and 99.1% w/w and lovastatin with a purity of 88.0% w/w and 98.8% w/w.

SUMMARY OF THE INVENTION

It is an object of the present invention to apply the process of the instant invention for the purification of HMG-CoA reductase inhibitors and to provide a purified HMG-CoA reductase inhibitor with high purity.

Other objects of this invention are to provide a composition of the HMG-CoA reductase inhibitor and a commercial scale composition of the HMG-CoA reductase inhibitor, each of them comprising the HMG-CoA reductase inhibitor and specific, reduced levels of impurities that are present in the said composition.

DETAILED DESCRIPTION OF SPECIFIC EMBODIMENTS

It is sometimes difficult to obtain the active substance of high purity in a large scale and/or a commercial scale as many technologies applicable to a laboratory scale are not sufficiently economical in large scale and/or commercial scale production operations to justify use thereof or do not meet the environmental criteria. The above facts compel the industry to search for new technologies that will provide both the high-quality product and the economically and ecologically acceptable production.

The present invention has solved the drawbacks of the processes known from the state of the art, including patent documents and other literature, as it enables to obtain the pure and/or purified HMG-CoA reductase inhibitors and, additionally, the purifying process per se is not time-consuming and provides high yields, using small amounts of solvents. The process is environmentally friendly; in addition, it is not demanding in terms of space and energy thus enabling an economical large scale and/or commercial scale production.

The present invention provides a process for the purification of HMG-CoA reductase inhibitors employing displacement chromatography. That means that at least one of the steps in the process of the purification of crude HMG-CoA reductase inhibitor includes displacement chromatography.

The HMG-CoA reductase inhibitor to be purified is, for example, selected from the group consisting of mevastatin, pravastatin, lovastatin, simvastatin, fluvastatin and atorvastatin. The selected inhibitor may be in the lactone form or in the form of the acid or the salt thereof for being purified by means of displacement chromatography. In the preferred embodiment of this invention the HMG-CoA reductase inhibitor to be purified is selected from the group consisting of pravastatin sodium salt, pravastatin lactone, simvastatin lactone, lovastatin lactone and mevastatin lactone.

The displacement chromatography being characteristic for the process of the present invention comprises the following steps: a) conditioning a chromatography column with an appropriate mobile phase, b) feeding the crude HMG-CoA reductase inhibitor dissolved in the mobile phase onto the chromatography column, c) introducing the displacer for displacing the HMG-CoA reductase inhibitor from the column, and d) obtaining the purified HMG-CoA reductase inhibitor.

In the preferred embodiment the displacement chromatography being characteristic for the process of the present invention has the following steps: a) conditioning a chromatography column with an appropriate mobile phase, b)

feeding the crude HMG-CoA reductase inhibitor dissolved in the mobile phase onto the chromatography column, c) introducing the displacer for displacing the HMG-CoA reductase inhibitor from the column, and d) obtaining the purified HMG-CoA reductase inhibitor.

The purified HMG-CoA reductase inhibitor is preferably obtained by: d1) collecting the fractions and d2) analyzing the fractions with analytical HPLC and pooling the fractions depending on the quality of purity.

After the purified HMG-CoA reductase inhibitor has been obtained, the chromatography column may be regenerated by washing of the column with alcohol/water mixture to elute the displacer.

HMG-CoA reductase inhibitors obtained in the herein-described manner are then isolated from the mobile phase according to the methods already known from the state of prior art, for example by lyophilization or, preferably, by crystallization to obtain the lactone form, the acid form or the salt form thereof. The preferred salt form of the HMG-CoA reductase inhibitor is a pharmaceutically acceptable salt of the HMG-CoA reductase inhibitor and most preferably an alkaline metal salt or an earth alkaline metal salt of the HMG-CoA reductase inhibitor. The most preferred salt form of the HMG-CoA reductase inhibitor is the sodium salt of pravastatin.

Within the scope of this invention the term an HMG-CoA reductase inhibitor with "a high purity" means an HMG-CoA reductase inhibitor with a high overall purity and/or an HMG-CoA reductase inhibitor with a reduced content of specific impurities.

Within the scope of this invention the term "composition" shall mean a composition comprised of an HMG-CoA reductase inhibitor and of the impurities that are present in it, wherein "an impurity" shall mean undesired side-products formed in or retained from the previous steps of the production process. The previous steps of the production process within the scope of this invention shall mean any production process for obtaining the HMG-CoA reductase inhibitors and may be selected from the group consisting of the biotechnological process, the process of the chemical synthesis and the process of semi-chemical synthesis as known in the art.

Within the scope of this invention the term "commercial scale composition" shall mean a commercial scale quantity of a composition, which may range from at least 100 g and to above 1000 g.

Within the scope of this invention the term "% area" shall mean a measurement unit or determination unit for defining an amount of a component compound contained in a composition. In one embodiment the % area can be determined based on analytical HPLC as described herein below by measuring the area of each individual peak and dividing the individual areas by the total sum of all the areas as determined by analytical HPLC. The formulae for determining the % area is thus the following:

% area=(area of individual component peak determined/total sum of all the areas of all the components determined)×100.

The term "below the limit of determination" or "below the determination limit" shall mean that a certain impurity is present in the composition in an amount of below 0.005% area. We were nevertheless in some cases of determination of impurities able to establish the limit of determination in the level at around 25 ppm.

The fractions containing a considerable percentage of HMG-CoA reductase inhibitors, in addition to impurities, may be re-subjected to the process resulting in the total yield exceeding 95%. In the preferred embodiment of this invention fractions are obtained containing a composition of the HMG-CoA reductase inhibitor or a commercial scale composition of the HMG-CoA reductase inhibitor comprising the HMG-CoA reductase inhibitor and specific, reduced levels of impurities that are present in the said composition. Such fractions may further be re-subjected to the process of the instant invention resulting in the composition of the HMG-CoA reductase inhibitor and/or in the commercial scale composition of the HMG-CoA reductase inhibitor with the total yield exceeding 95% and a high overall purity and with reduced levels of impurities that are present in the said composition.

In the most preferred embodiment of this invention the obtained fraction of the composition of pravastatin sodium salt and/or of the commercial scale composition of pravastatin sodium salt consists of pravastatin sodium salt and reduced levels of impurities. Pravastatin sodium salt is chemically (aR,bR,1S,2S,6S,8S,8aR)-1,2,6,7,8,8a-hexahydro-b,d,6-trihydroxy-2-methyl-8-((2S)-2-methyl-1-oxobutoxy)-1-naphthaleneheptanioic acid monosodium salt.

In a more preferred embodiment the said composition of pravastatin sodium salt and/or the said commercial scale composition of pravastatin sodium salt composition consists of pravastatin sodium salt and a reduced level of at least one impurity selected from the group consisting of:

(aR,bR,1S,2S,6S,8S,8aR)-1,2,6,7,8,8a-hexahydro-b,d,6-trihydroxy-2-methyl-8-hydroxy-1-naphthaleneheptanioic acid monosodium salt, which has a structural Formula A and is herein referred to as impurity A;

(aR,bR,1S,2S,6R,8S,8aR)-1,2,6,7,8,8a-hexahydro-b,d,6-trihydroxy-2-methyl-8-hydroxy-1-naphthaleneheptanioic acid monosodium salt, which has a structural Formula D and is herein referred to as impurity D;

(aR,bR,1S,2S,6S,8S,8aR)-1,2,6,7,8,8a-Hexahydro-b,d,(6S)-6-trihydroxy-2-methyl-8-((2S)-2-methyl-(3S)-3-hydroxy-1-oxobutoxy)-1-naphthaleneheptanioic acid monosodium salt, which has a structural Formula E and is herein referred to as impurity E;

(aR,bR,1S,2S,6S,8S,8aR)-1,2,6,7,8,8a-hexahydro-b,d,6-trihydroxy-2-methyl-8-((2S)-2-methyl-(3R)-3-hydroxy-1-oxobutoxy)-1-naphthaleneheptanioic acid monosodium salt, which has a structural Formula F and is herein referred to as impurity F;

(aR,bR,1S,2S,6R)-1,2-dihydro-b,d,6-trihydroxy-2-methyl-1-naphthaleneheptanioic acid monosodium salt, which has a structural Formula G and is herein referred to as impurity G;

(aR,bR,1S,2S,6S,8aR)-1,2,6,7,8,8a-hexahydro-b,d,6-trihydroxy-2-methyl-1-naphthaleneheptanioic acid monosodium salt, which has a structural Formula I and is herein referred to as impurity I;

(aR,bR,1S,2S,6R,8S,8aR)-1,2,6,7,8,8a-hexahydro-b,d,6-trihydroxy-2-methyl-8-((2S)-2-methyl-1-oxobutoxy)-1-naphthaleneheptanioic acid monosodium salt, which has a structural Formula K and is herein referred to as impurity K;

(aR,bR,1S,2S,6S,8S,8aR)-1,2,6,7,8,8a-hexahydro-b,d,6-trihydroxy-2-methyl-8-((2S)-2-methyl-1-oxo-2-3-en-butoxy)-1-naphthaleneheptanioic acid monosodium salt, which has a structural Formula M and is herein referred to as impurity M;

(aR,bR,1S,2S,8S,8aR)-1,2,6,7,8,8a-hexahydro-b,d,3-trihydroxy-2-methyl-8-((2S)-2-methyl-1-oxobutoxy)-1-naphthaleneheptanioic acid monosodium salt, which has a structural Formula N and is herein referred to as impurity N;

(aR,bR,1S,2S,6S,8S,8aR)-1,2,6,7,8,8a-hexahydro-b,d,6-trihydroxy-2-methyl-8-((2S)-2-methyl-1-oxopentoxy)-1-naphthaleneheptanioic acid monosodium salt, which has a structural Formula O and is herein referred to as impurity O;

a combination herein referred to as impurity T, which consists of two impurities herein referred to as impurity T1 and impurity T2, which have a structural Formula T1 and a structural Formula T2, respectively, wherein impurity T1 is chemically (aR,bR,1S,2S,8S,8aR)-1,2,6,7,8,8a-hexahydro-b,d-dihydroxy-2-methyl-8-((2S)-2-methyl-3-hydroxy-1-oxobutoxy)-1-naphthaleneheptanioic acid monosodium salt and impurity T2 is chemically (aR,bR,1S,2S,8S,8aR)-1,2,6,7,8,8a-hexahydro-b,d-dihydroxy-2-methyl -8-((2S)-2-methyl-3-hydroxy-1-oxobutoxy)-1-naphtholeneheptanioic acid monsodium salt and ipurity T2 is chemically (aR,bR,1S,2S,8S,8aR)-1,2,6,7,8,8a-hexa-hydro-b,d-dihydroxy-2-methyl-8-((2S)-2-methyl-4-hydroxy-1-oxobutoxy)-1-naphtalennheptanioic acid monosodium salt. In the herein described analysis by the HPLC method (see Example 3) both of these impurities T1 and T2 are displaced in one peak.

The components of the composition of pravastatin sodium salt and/or of the commercial scale composition of pravastatin sodium salt have the following formulae.

Pravastatin:

D:

E:

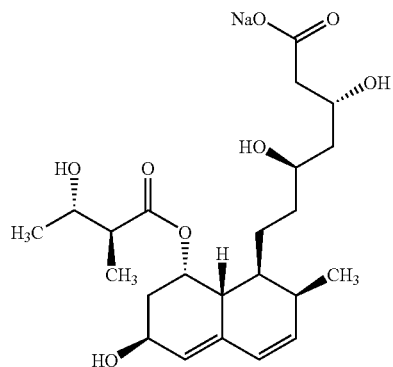

F:

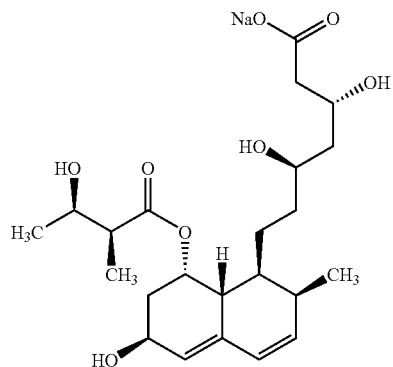

G:

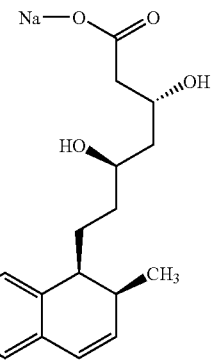

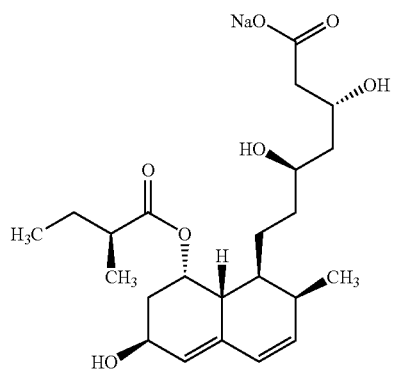

I:

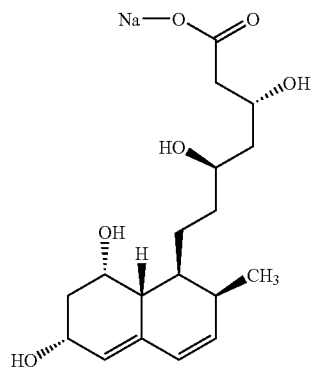

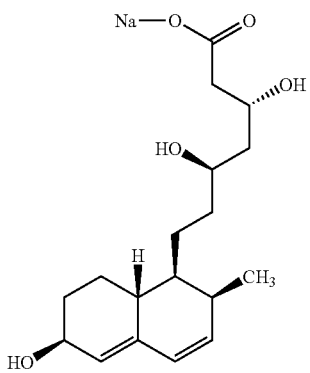

A:

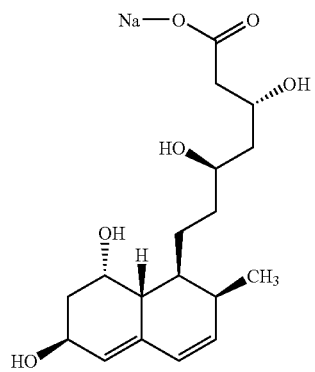

K:

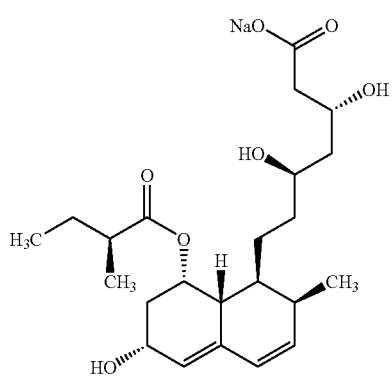

M:

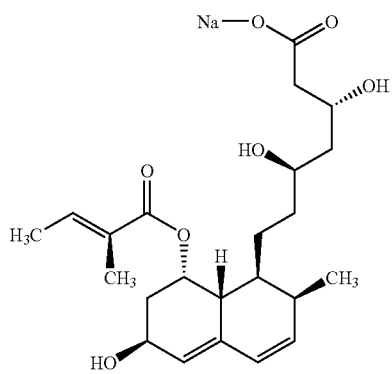

N:

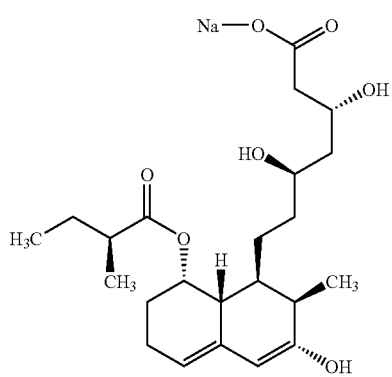

O:

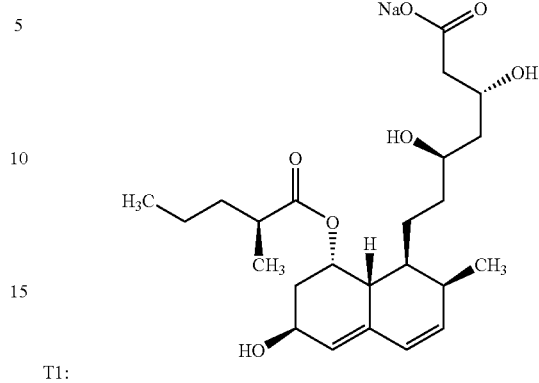

T1:

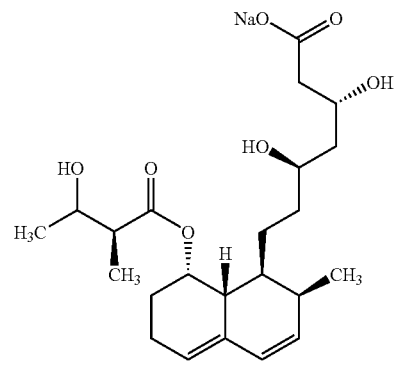

T2:

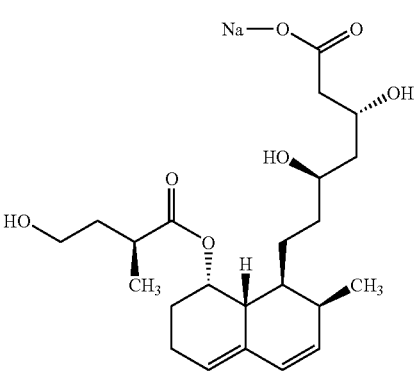

The obtained purified composition of pravastatin sodium salt and/or commercial scale composition of pravastatin sodium salt consists of pravastatin sodium salt in an amount of at least 99.7% area and of reduced levels of the respective impurities in a total amount of below 0.3% area. In the said purified composition of pravastatin sodium salt and/or commercial scale composition of pravastatin sodium salt the respective impurities are present in amounts as follows:

(aR,bR,1S,2S,6S,8S,8aR)-1,2,6,7,8,8a-hexahydro-b,d,6-trihydroxy-2-methyl-8-hydroxy-1-naphthaleneheptanioic acid monosodium salt in an amount of below the limit of determination; and/or (aR,bR,1S,2S,6R,8S,8aR)-1,2,6,7,8,8a-hexahydro-b,d,6-trihydroxy-2-methyl-8-hydroxy-1-naphthaleneheptanioic acid monosodium salt in an amount of below 0.01% area; and/or (aR,bR,1S,2S,6S,8S,8aR)-1,2,6,7,8,8a-Hexahydro-b,d,6-trihydroxy-2-methyl-8-((2S)-2-methyl-(3S)-3-hydroxy-1- oxobutoxy)-1-naphthaleneheptanioic acid monosodium salt in an amount of below 0.01% area; and/or (aR,bR,1S,2S,6S,8S,8aR)-1,2,6,7,8,8a-hexahydro-b,d,6-trihydroxy-2-methyl-8-((2S)-2-methyl-(3S)-3-hydroxy-1-oxobutoxy)-1-naphthaleneheptanioic acid monsodium salt in an amount of below the limit of determination; and/or (aR,bR,1S,2S,6R)-1,2-dihydro-b,d,6-trihydroxy-2-methyl-1-naphthaleneheptanioic acid monosodium salt in an amount of below 0.01% area; and/or (aR,bR,1S,2S,6S,8aR)-1,2,6,7,8,8a-hexahydro-b,d,6-trihydroxy-2-methyl-1-naphthaleneheptanioic acid monosodium salt in an amount of below 0.1% area; and/or (aR,bR,1S,2S,6R,8S,8aR)-1,2,6,7,8,8a-hexahydro-b,d,6-trihydroxy-2-methyl-8-((2S)-2-methyl-1-oxobutoxy)-)-1-naphthaleneheptanioic acid monosodium salt in an amount of below 0.1% area; and/or (aR,bR,1S,2S,6S,8S,8aR)-1,2,6,7,8,8a-hexahydro-b,d,6-trihydroxy-2-methyl-8-((2S)-2-methyl-1-oxo-2-3-en-butoxy)-1-naphthaleneheptanioic acid monosodium salt in an amount of below 0.1% area; and/or (aR,bR,1S,2S,8S,8aR)-1,2,6,7,8,8a-hexahydro-b,d,3-trihydroxy-2-methyl-8-((2S)-2-methyl-1-oxobutoxy)-1-naphthaleneheptanioic acid monosodium salt in an amount of below 0.05% area; and/or (aR,bR,1S,2S,6S,8S,8aR)-1,2,6,7,8,8a-hexahydro-b,d,6-trihydroxy-2-methyl-8-((2S)-2-methyl-1-oxopentoxy)-1-naphthaleneheptanioic acid monosodium salt in an amount of below the limit of determination; and/or a total sum of impurities (aR,bR,1S,2S,8S,8aR)-1,2,6,7,8,8a-hexahydro-b,d-dihydroxy-2-methyl-8-((2S)-2-methyl-3-hydroxy-1-oxobutoxy)-1-naphthaleneheptanioic acid monosodium salt and (aR,bR,1S,2S,8S,8aR)-1,2,6,7,8,8a-hexahydro-b,d-dihydroxy-2-methyl-8-( (2S)-2-methyl-4-hydroxy-1-oxobutoxy)-1-naphtalennheptanioic acid monosodium salt in an amount of below the limit of determination; and/or the total sum of unidentified impurities in an amount of below the limit of determination.

The starting material for the instant purification process is the respective crude HMG-CoA reductase inhibitor and/or crude composition of the HMG-CoA reductase inhibitor and/or crude commercial scale composition of the HMG-CoA reductase inhibitor, which consists of the said HMG-CoA reductase inhibitor and a certain amount of the total sum of the impurities expressed in % area and certain amounts of individual impurities expressed in % area, which are reduced by the said purification process. An overall purity of the crude HMG-CoA reductase inhibitor and/or of the crude composition of the HMG-CoA reductase inhibitor and/or of the crude commercial scale composition of the HMG-CoA reductase inhibitor is preferably above 80% area and more preferably above 85% area, wherein the total amount of the impurities present is around or below 20% area and preferably around or below 15% area.

The stationary phase used is a reverse phase where natural (silica gel with alkyl chains of a different length) or synthetic (C-18 or C-8 organic) stationary phases are suitable. Preferably, a synthetic cross-linked polymer matrix of styrene and divinylbenzene is used. The particle size of the stationary phase is suitably from 3 to 20 μm, preferably between 7 and 15 μm.

The mobile phase used is preferably selected from water, acetonitrile/water solution and aqueous solutions of lower (preferably C1–C4) alcohols, buffered dilute solutions of organic, halogenated organic or inorganic acids, e.g. formic, acetic, propionic, hydrochloric, boric, phosphoric, carbonic or sulfuric acids with cations of alkaline metals, with ammonia or with amines. Water and aqueous solutions with acetonitrile and especially with methanol or ethanol are particularly preferred, and the content of the organic solvent in the aqueous solutions preferably is 80% or below, more preferably 45% or below and particularly 30% or below. Since toxic methanol in the mobile phase may be replaced by less toxic ethanol, or may be at least partially replaced by water with good results, removal of waste solvents is simpler, therefore, the present invention is a marked improvement compared to the state of prior art judging from the ecological aspect.

The pH of the mobile phase used is preferably between 4.5 and 10.5, more preferably between 6.5 and 8, and particularly around 7. The flow rate of the mobile phase through the column is suitably adjusted to lie between 1.5 and 30 mL/(min·cm$^2$), preferably between 3 and 15 mL/(min·cm$^2$). At the time when the displacer is introduced into the chromatography column by being mixed with the mobile phase, the flow rate is preferably adjusted to lie between 1.5 and 15 mL/(min·cm$^2$) and particularly between 3 and 10 ml/(min·cm$^2$), because higher flow rates cause the dilution of the samples to be collected, and also the separation becomes worse.

The displacer suitably is a compound having an amphiphilic structure, such as surfactants, detergents and the like.

Examples of the displacer are long chain alcohols, long chain carboxylic acids, long chain alkyl ammonium salts, aromatic dicarboxylic acid esters, oxo- and dioxoalcohols, polyalkylene polyglycol ethers such as diethylene glycol mono- (or di-)alkylethers, polyaryl or polyalkylene polyaryl ethers such as Triton® X-100, etc.

The aforementioned "long chain" means an alkyl chain having at least a C4-chain, preferably at least a C10-chain and more preferably at least a C14-chain or longer.

The concentration of the displacer in the mobile phase is suitably adjusted to be from 1 to 35%, preferably from 2 to 20% and particularly from 7 to 14%.

In the preferred embodiment of controlling the quality of purity in the individual fractions eluted from the chromatography column, an analytical HPLC method directed to the HMG-CoA reductase inhibitors to be analyzed may be carried out as described in the following.

The sample to be analyzed is diluted 100 times with the mobile phase containing 20 mM aqueous NH$_4$HCO$_3$ solution with acetonitrile (the proportion of acetonitrile is adjusted such that the retention factor of the analyte is between 5 and 10). 10 μL of this sample is placed on Hypersil ODS column (Hypersil, the United Kingdom, particle size 3 μm, column size 50×4.6 mm) for high performance liquid chromatography. The column is washed with the mobile phase at the flow rate of 2 mL/min. Absorbance is measured at 235 nm. HPLC purity of the sample is calculated from the ratio between the areas of individual peaks and the sum of the areas of all the peaks in the chromatogram.

After completed chromatography the stationary phase is preferably regenerated, for example using the mobile phase with 20 to 100% aqueous solution of lower alcohol.

The invention is illustrated but in no way limited by the following examples.

EXAMPLES

Example 1

Crude sodium salt of pravastatin (1.0 g, HPLC purity 88%, assay 85%) was dissolved in 10 mL of the mobile phase A (distilled water), pH was adjusted to 7 with 0.2M aqueous NaOH solution and filtered. The column was equilibrated with mobile phase A. The sample obtained in the above-described manner was fed onto the Grom-Sil 120-ODS HE column (Grom Analytic+HPLC GmbH, Germany), particle size 11 µm, column size 250×10 mm. The column was washed with the mobile phase B containing 7% of diethyleneglycol monobutylether in mobile phase A at the flow rate of 4.5 mL/min. Absorbance was measured at 260 nm, and the 0.5 mL fractions were collected with an initial increase in the absorbance. When the signal decreased the column was washed with 25 mL of 70% methanol. The obtained fractions were analyzed by the herein above-described HPLC analytical method. The fractions with a purity≧99.5% were pooled. In the pooled fractions (7 mL) the HPLC purity was 99.8%.

Example 2

Crude sodium salt of pravastatin (0.4 g, HPLC purity 88%, assay 85%) was dissolved in 5 mL of the mobile phase A (distilled water), pH was adjusted to 7 with 0.2M aqueous NaOH solution and filtered. The column was equilibrated with mobile phase A. The sample obtained in the above-described manner was fed onto the Kromasil 100 C-18 column (EKA Chemicals AB, Sweden), particle size 10 µm, column size 200×10 mm. The column was washed with the mobile phase B containing 7% of Triton X-100 in mobile phase A at the flow rate of 1 mL/min. Absorbance was measured at 260 nm, and the 0.5 mL fractions were collected with an initial increase in the absorbance. The obtained fractions were analyzed by the above described HPLC analytical method. The fractions with a purity≧99.5% were pooled. In the pooled fractions (3 mL) the HPLC purity was 99.7%.

Example 3

0.6 g of the crude sodium salt of pravastatin (HPLC purity 85.43%, assay 85%) was dissolved in 5 mL of distilled water. The protocol described in Example 1 was used with the exception of the mobile phase used (30% aqueous methanol solution) and the pooled fractions with a HPLC purity of 99.8% were obtained.

The pooled fractions and the crude (load) sodium salt of pravastatin were analyzed using the following HPLC method:

A linear gradient was used with two mobile phases consisting of: A=2.5 mM phosphoric buffer, pH 7.0 with added 14% (v/v) acetonitrile and B=2.5 mM phosphoric buffer, pH 7.0 with added 80% (v/v) acetonitrile. The flow rate was 2 mL/min and the column was Hypersil ODS (Hypersil, United Kingdom, particle size 3 µm, column size 100×4.6 mm).

The column was stabilized for 4 min with mobile phase composition of 96% A, 6% B then 5 µl of sample was injected and after 5 min a linear gradient to 88% A, 12% B was applied till the $7^{th}$ min, then a linear gradient to 60% A, 40% B was applied till the $12^{th}$ min. Absorbance was measured at 235 nm for 14 min. The crude pravastatin sodium salt was dissolved in mobile phase A at the concentration of 1 mg/mL, the pooled fractions were diluted 100 times with mobile phase A.

The HPLC purity of the samples was calculated from the ratio of the areas of individual peaks and the sum of all the areas (area %). The retention time of pravastatin sodium salt was about 5 min.

By this analytical method the content of each of the above described impurities A, D, E, F, G, I, K, M, N, O and T was also determined: the determined amounts are listed in Table 1 below.

TABLE 1

Crude and purified composition of pravastatin sodium salt

| component | Crude composition before purification with the process of this invention Determined amount in % area | Purified composition After purification with the process of this invention Determined amount in % area |
| --- | --- | --- |
| Pravastatin sodium salt | 85.430 | 99.780 |
| Impurity A | 0.265 | Below the determination limit |
| Impurity D | 3.438 | 0.007 |
| Impurity E | 0.209 | 0.005 |
| Impurity F | 0.165 | Below the determination limit |
| Impurity G | 0.171 | 0.005 |
| Impurity I | 0.528 | 0.064 |
| Impurity K | 3.977 | 0.062 |
| Impurity M | 0.193 | 0.054 |
| Impurity N | 1.049 | 0.023 |
| Impurity O | 0.105 | Below the determination limit |
| Impurities T (total sum of impurities T1 and T2, which are displaced in one peak) | 1.726 | Below the determination limit |
| Total sum of unidentified impurities | 2.439 | Below the determination limit |

Example 4

The method described in Example 3 was repeated wherein the concentration of the displacer in the mobile phase was 14%. In the fractions pooled, according to the criterion described in Example 1, HPLC purity was 99.8%.

Example 5

Pravastatin lactone (0.4 g, HPLC purity 85%) was dissolved in 33 mL of the mobile phase A containing 45% methanol. The column was equilibrated with mobile phase A. The sample obtained in the above-described manner was fed onto the Grom-Sil 120-ODS HE column (Grom Analytic+HPLC GmbH, Germany), particle size 11 µm, column size 250×10 mm.

The column was washed with the mobile phase B containing 2% of diethyleneglycol dibutylether in mobile phase A at the flow rate of 4.5 mL/min. Absorbance was measured at 260 nm, and the 1 mL fractions were collected with an initial increase in the absorbance. When the signal decreased the column was washed with 25 ml of 70% methanol. The

Example 6

Pravastatin lacton (0.3 g, HPLC purity 85%) was dissolved in 80 mL of the mobil phase A containing 30% methanol. The column was equilibrated with mobile phase A. The sample obtained in the above-described manner was fed onto the Licrosphere RP 18 column, particle size 12 μm, column size 200×10 mm. The column was washed with the mobile phase B containing 5% of diethyleneglycolmono-n-hexylether in mobile phase A at the flow rate of 4.5 mL/min. Absorbance was measured at 235 nm, and the 1 mL fractions were collected with an initial increase in the absorbance. When the signal decreased the column was washed with 25 mL of 90% methanol. The obtained fractions were analyzed by the above described HPLC analytical method. The fractions with a purity≧99.5% were pooled. In the pooled fractions the HPLC purity was 99.8%.

Example 7

Pravastatin lactone (0.3 g, HPLC purity 85%) was dissolved in 25 mL of the mobile phase A containing 35% acetonitrile.

The column was equilibrated with mobile phase A. The sample obtained in the above-described manner was fed onto the Licrosphere RP 18 column, particle size 12 pm, column size 200×10 mm. The column was washed with the mobile phase B containing 1% of diethyleneglycol dibutylether in mobile phase A at the flow rate of 4.5 mL/min.

Absorbance was measured at 235 nm, and the 1 mL fractions were collected with an initial increase in the absorbance. When the signal decreased the column was washed with 25 mL of 90% methanol. The obtained fractions were analyzed by the above described HPLC analytical method.

The fractions with a purity≧99.5% were pooled. In the pooled fractions the HPLC purity was 99.8%.

Example 8

The method described in Example 7 was repeated wherein the mobile phase B was 0.85% diethylphthalate in the mobile phase A.

The fractions with a purity≧99.5% were pooled. In the pooled fractions the HPLC purity was 99.8%.

Example 9

Simvastatin lactone (0.42 g, HPLC purity 87%) was dissolved in 6 mL of the 66% acetonitrile and hydrolyzed with 1.2 mmol of sodium hydroxide. Acetonitrile was removed and pH was adjusted to 7 with diluted $H_3PO_4$. The column was equilibrated with mobile phase A containing 14% of methanol. The sample obtained in the above-described manner was fed onto the Grom-Sil 120-ODS HE column (Grom Analytic+HPLC GmbH, Germany), particle size 11 μm, column size 250×10 mm. The column was washed with the mobile phase B containing 6.7% of diethyleneglycol mono-n-hexylether in mobile phase A at the flow rate of 4.5 mL/min. Absorbance was measured at 260 nm, and the 0.5 mL fractions were collected with an initial increase in the absorbance. When the signal decreased the column was washed with 25 mL of methanol.

The fractions with a purity≧99.5% were pooled. In the pooled fractions the HPLC purity was 99.8%.

Example 10

Simvastatin lactone (0.5 g, HPLC purity 87%) was dissolved in 20 mL of the mobile phase containing 70% of methanol.

The column was equilibrated with mobile phase A. The sample obtained in the above-described manner was fed onto the Grom-Sil 120-ODS HE column (Grom Analytic+HPLC GmbH, Germany), particle size 11 μm, column size 250×10 mm.

The column was washed with the mobile phase B containing 3% of decanoic acid in mobile phase A at the flow rate of 4.5 mL/min. Absorbance was measured at 260 nm, and the 0.75 mL fractions were collected with an initial increase in the absorbance. When the signal decreased the column was washed with 25 mL of methanol. The obtained fractions were analyzed by the herein above described method. The fractions with a purity≧99.5% were pooled. In the pooled fractions the HPLC purity was 99.7%.

Example 11

Simvastatin lactone (0.5 g, HPLC purity 87%) was dissolved in 20 mL of the mobile phase containing of 60% acetonitrile. The column was equilibrated with mobile phase A. The sample obtained in the above-described manner was fed onto the Grom-Sil 120-ODS HE column (GroM Analytic+HPLC GmbH, Germany), particle size 11 μm, column size 250×10 mm. The column was washed with the mobile phase B containing 2% of tetrakis(decyl)ammonium bromide in mobile phase A at the flow rate of 4.5 mL/min. Absorbance was measured at 260 nm, and the 1 mL fractions were collected with an initial increase in the absorbance. When the signal decreased the column was washed with 25 mL of methanol.

The fractions with a purity≧99.5% were pooled. In the pooled fractions the HPLC purity was 99.8%.

Example 12

Lovastatin lactone (0.5 g, HPLC purity 87%) was dissolved in 60 mL of the 75% methanol. The column was equilibrated with mobile phase A containing 70% of methanol. The sample obtained in the above-described manner was fed onto the Grom-Sil 120-ODS HE column (Grom Analytic+HPLC GmbH, Germany), particle size 11 μm, column size 250×10 mm.

The column was washed with the mobile phase B containing 70% of methanol and 4.5% of decanoic acid in mobile phase A at the flow rate of 6 mL/min. Absorbance was measured at 260 nm, and the 1 mL fractions were collected with an initial increase in the absorbance. When the signal decreased the column was washed with 25 mL of methanol.

The obtained fractions were analyzed by the above described HPLC analytical method. The fractions with a purity≧99.5% were pooled. In the pooled fractions the HPLC purity was 99.9%.

Example 13

Lovastatin lactone (0.42 g, HPLC purity 87%) was dissolved in 8 mL of the 50% acetonitrile and hydrolyzed with 1.5 mmol of sodium hydroxide. Acetonitrile was removed and pH was adjusted to 7 with diluted H₃PO₄. The column was equilibrated with mobile phase A containing 14% of methanol. The sample obtained in the above-described manner was fed onto the Grom-Sil 120-ODS HE column (Grom Analytic+HPLC GmbH, Germany), particle size 11 μm, column size 250×10 mm. The column was washed with the mobile phase B containing 6.7% of diethyleneglycolmono-n-hexylether in mobile phase A at the flow rate of 1 mL/min.

Absorbance was measured at 260 nm, and the 0.25 mL fractions were collected with an initial increase in the absorbance. When the signal decreased the column was washed with 25 mL of methanol.

The obtained fractions were analyzed by the method described in example 9. The fractions with a purity≧99.5% were pooled. In the pooled fractions the HPLC purity was 99.8%.

Example 14

Mevastatin lactone (0.5 g, HPLC purity 85%) was dissolved in 150 mL of the mobile phase A containing 70% of methanol.

The column was equilibrated with mobile phase A. The sample obtained in the above-described manner was fed onto the Grom-Sil 120-ODS HE column (Grom Analytic+ HPLC GmbH, Germany), particle size 11 μm, column size 250×10 mm.

The column was washed with the mobile phase B containing 4.5% of decanoic acid in mobile phase A at the flow rate of 6 mL/min. Absorbance was measured at 260 nm, and the 1 mL fractions were collected with an initial increase in the absorbance. When the signal decreased the column was washed with 25 mL of methanol.

The obtained fractions were analyzed by the above described HPLC analytical method.

The fractions with a purity≧99.5% were pooled. In the pooled fractions the HPLC purity was 99.8%.

Example 15

Crude sodium salt of pravastatin (700 g, HPLC purity 88%, assay 85%) was dissolved in 7 L of the mobile phase A (distilled water), pH was adjusted to 7 with 0.2M aqueous NaOH solution and filtered. The column was equilibrated with mobile phase A. The sample obtained in the above-described manner was fed onto the Grom-Sil 120-ODS HE column (Grom Analytic+HPLC GmbH, Germany), particle size 11 μm, column size 250×300 mm (column type HIP-ERSEP LC300; Nova Sep S.A.S., Pompey, France). The column was washed with the mobile phase B containing 7% of diethyleneglycol monobutylether in mobile phase A at the flow rate of 4L/min. Absorbance was measured at 260 nm, and the 0.5 L fractions were collected with an initial increase in the absorbance. When the signal decreased the column was washed with 23 L of 70% methanol. The obtained fractions were analyzed by the herein above-described HPLC analytical method. The fractions with a purity≧99.5% were pooled. In the pooled fractions the HPLC purity was 99.7%.

What is claimed is:

1. A composition of a purified HMG-CoA reductase inhibitor having a purity of at least 99.7%, the composition consisting of pravastatin sodium salt and a total level of impurity of not more than 0.3%, wherein the total level of impurity includes a reduced level of at least one impurity selected from the group consisting of:

(aR,bR,1S,2S,6S,8S,8aR)-1,2,6,7,8,8a-hexahydro-b,d,6-trihydroxy-2-methyl-8-hydroxy-1-naphtaleneheptanioic acid monosodium salt, (aR,bR,1S,2S,6R,8S,8aR)-1,2,6,7,8,8a-hexahydro-b,d,6-trihydroxy-2-methyl-8-hydroxy-1-naphtaleneheptanioic acid monosodium salt, (aR,bR,1S,2S,6S,8S,8aR)-1,2,6,7,8,8a-hexahydro-b,d,6-trihydroxy-2-methyl-8-((2S)-2-methyl-(3S)-3-hydroxy-1-oxobutoxy)-1-naphtaleneheptanioic acid monosodium salt, (aR,bR,1S,2S,6S,8S,8aR)-1,2,6,7,8,8a-hexahydro-b,d,6-trihydroxy-2-methyl-8-((2S)-2-methyl-(3R)-3-hydroxy-1-oxobutoxy)-1-naphtaleneheptanioic acid monosodium salt, (aR,bR,1S,2S,6R)-1,2-dihydro-b,d,6-trihydroxy-2-methyl-1-naphtaleneheptanioic acid monosodium salt, (aR,bR,1S,2S,6S,8aR)-1,2,6,7,8,8a-hexahydro-b,d,6-trihydroxy-2-methyl-1-naphtaleneheptanioic acid monosodium salt, (aR,bR,1S,2S,6R,8S,8aR)-1,2,6,7,8,8a-hexahydro-b,d,6-trihydroxy-2-methyl-8-((2S)-2-methyl-1-oxobutoxy)-1-naphtaleneheptanioic acid monosodium salt, (aR,bR,1S,2S,6S,8S,8aR)-1,2,6,7,8,8a-hexahydro-b,d,6-trihydroxy-2-methyl-8-((2S)-2-methyl-1-oxo-2-3-en-butoxy)-1-naphtaleneheptanioic acid monosodium salt, (aR,bR,1S,2S,8 S,8aR)-1,2,6,7,8,8a-hexahydro-b,d,3-trihydroxy-2-methyl-8-((2S)-2-methyl-1-oxobutoxy)-1-naphtaleneheptanioic acid monosodium salt, (aR,bR,1S,2S,6S,8S,8aR)-1,2,6,7,8,8a-hexahydro-b,d,6-trihydroxy-2-methyl-8-((2S)-2-methyl-1-oxopentoxy)-1-naphtaleneheptanioic acid monosodium salt, (aR,bR,1 S,2S,8S,8aR)-1,2,6,7,8,8a-hexahydro-b,d-dihydroxy-2-methyl-8-((2S)-2-methyl-3-hydroxy-1-oxobutoxy)-1-naphtaleneheptanioic acid monosodium salt, and (aR,bR,1S,2S,8S,8aR)-1,2,6,7,8,8a-hexahydro-b,d-dihydroxy-2-methyl-8-((2S)-2-methyl-4-hydroxy-1-oxobutoxy)-1-naphtalennheptanioic acid monosodium salt.

2. A composition of pravastatin sodium salt according to claim 1, wherein an individual impurity selected from the group consisting of:

(aR,bR,1S,2S,6S,8S,8aR)-1,2,6,7,8,8a-hexahydro-b,d,6-trihydroxy-2-methyl-8-hydroxy-1-naphtaleneheptanioic acid monosodium salt, (aR,bR,1S,2S,6S,8S,8aR)-1,2,6,7,8,8a-hexahydro-b,d,6-trihydroxy-2-methyl-8-((2S)-2-methyl-(3R)-3-hydroxy-1-oxobutoxy)-1-naphtaleneheptanioic acid monosodium salt, (aR,bR,1S,2S,6S,8S,8aR)-1,2,6,7,8,8a-hexahydro-b,d,6-trihydroxy-2-methyl-8-((2S)-2-methyl-1-oxopentoxy)-1-naphtaleneheptanioic acid monosodium salt, (aR,bR,1S,2S,8S,8aR)-1,2,6,7,8,8a-hexahydro-b,d-dihydroxy-2-methyl-8-((2S)-2-methyl-3-hydroxy-1-oxobutoxy)-1-naphtaleneheptanioic acid monosodium salt, and (aR,bR,1S ,2S,8S,8aR)-1,2,6,7,8,8a-hexahydro-b,d-dihydroxy-2-methyl-8-((2S)-2-methyl-4-hydroxy-1-oxobutoxy)-1-naphtalennheptanioic acid monosodium salt, is present in an amount of below the limit of determination.

3. A composition of pravastatin sodium salt according to claim 1, wherein an individual impurity selected from the group consisting of:

(aR,bR,1S,2S,6R,8S,8aR)-1,2,6,7,8,8a-hexahydro-b,d,6-trihydroxy-2-methyl-8-hydroxy-1-naphtaleneheptanioic acid monosodium salt, (aR,bR,1S,2S,6S,8S,8aR)-1,2,6,7,8,8a-Hexahydro-b,d,6-trihydroxy-2-methyl-8-((2S)-2-methyl-(3S)-3-hydroxy-1-oxobutoxy)-1-naphtaleneheptanioic acid monosodium salt, and (aR,bR,1S,2S,6R)-1,2-dihydro-b,d,6-trihydroxy-2-methyl-1-naphtaleneheptanioic acid monosodium salt, is present in an amount of below 0.01% area.

4. A composition of pravastatin sodium salt according to claim 1, wherein an individual impurity selected from the group consisting of:

(aR,bR,1S,2S,6S,8aR)-1,2,6,7,8,8a-hexahydro-b,d,6-trihydroxy-2-methyl-1-naphtaleneheptanioic acid monosodium salt, (aR,bR,1S,2S,6R,8S,8aR)-1,2,6,7,8,8a-hexahydro-b,d,6-trihydroxy-2-methyl-8-((2S)-2-methyl-1-oxobutoxy)-1-naphtaleneheptanioic acid monosodium salt, and (aR,bR,1S,2S,6S,8S,8aR)-1,2,6,7,8,8a-hexahydro-b,d,6-trihydroxy-2-methyl-8-((2S)-2-methyl-1-oxo-2-3-en-butoxy)-1-naphtaleneheptanioic acid monosodium salt, is present in an amount of below 0.1% area.

5. A composition of pravastatin sodium salt according to claim 1, wherein the impurity (aR,bR,1S,2S,8S,8aR)-1,2,6,7,8,8a-hexahydro-b,d,3-trihydroxy-2-methyl-8-((2S)-2-methyl-1-oxobutoxy)-1-naphtaleneheptanioic acid monosodium salt is present in an amount of below 0.05% area.

* * * * *